(12) United States Patent
Lyon et al.

(10) Patent No.: US 9,523,650 B2
(45) Date of Patent: Dec. 20, 2016

(54) SPRING LOADED EXHAUST GAS TEMPERATURE SENSOR ASSEMBLY

(71) Applicant: Conax Technologies LLC, Buffalo, NY (US)

(72) Inventors: Richard A. Lyon, Clarence, NY (US); Thomas P. Oakley, Jr., Buffalo, NY (US); Steven M. Dale, Clarence, NY (US)

(73) Assignee: Conax Technologies LLC, Buffalo, NY (US)

( * ) Notice: Subject to any disclaimer, the term of this patent is extended or adjusted under 35 U.S.C. 154(b) by 485 days.

(21) Appl. No.: 14/020,581

(22) Filed: Sep. 6, 2013

(65) Prior Publication Data

US 2015/0068281 A1    Mar. 12, 2015

(51) Int. Cl.
| | |
|---|---|
| *G01N 25/00* | (2006.01) |
| *G01M 15/10* | (2006.01) |
| *G01K 1/10* | (2006.01) |
| *G01K 1/14* | (2006.01) |
| *G01K 13/02* | (2006.01) |

(52) U.S. Cl.
CPC .............. *G01N 25/00* (2013.01); *G01K 1/10* (2013.01); *G01K 1/14* (2013.01); *G01K 13/02* (2013.01); *G01M 15/102* (2013.01); *G01K 2205/04* (2013.01)

(58) Field of Classification Search
CPC ........ G01N 25/00; G01M 15/102; G01K 1/10; G01K 1/14; G01K 13/02; G01K 2205/04
USPC .......................................... 374/100; 73/25.01
See application file for complete search history.

(56) References Cited

U.S. PATENT DOCUMENTS

| | | | | |
|---|---|---|---|---|
| 4,355,912 A | * | 10/1982 | Haak ........................ | G01K 1/14 374/208 |
| 4,448,546 A | * | 5/1984 | Paros ....................... | G01K 7/32 310/361 |
| 5,632,557 A | * | 5/1997 | Simons .................... | G01K 1/08 374/148 |

(Continued)

OTHER PUBLICATIONS

Conax Buffalo Technologies, Exhaust Gas Thermocouples 362A1102, Bulletin 6054 (2005).

(Continued)

*Primary Examiner* — Lisa Caputo
*Assistant Examiner* — Philip Cotey

(57) ABSTRACT

An improved temperature sensor assembly (15) comprising a temperature sensing probe (16) having a temperature sensing portion (18), a terminal portion (21), and an intermediate portion (20) between the temperature sensing portion and the terminal portion; a mounting element (28) in sliding engagement along a first axis (x-x) with the intermediate portion of the temperature sensing probe such that the temperature sensing probe is movable linearly relative to the mounting element in an axial direction; the mounting element configured to attach to an open tip thermowell (100) such that the temperature sensing portion of the probe is exposed to a process environment (104); the temperature sensing probe comprising a stop (19) configured to bear against a seat (108) in the thermowell; and a spring element (24) arranged between the stop and the mounting element and configured to bias the stop and the mounting element linearly away from each other in the axial direction.

30 Claims, 6 Drawing Sheets

(56) References Cited

U.S. PATENT DOCUMENTS

| | | | | |
|---|---|---|---|---|
| 5,674,009 A * | 10/1997 | Stark | | G01K 1/08 |
| | | | | 136/230 |
| 6,220,749 B1 * | 4/2001 | Wyker | | F16C 37/00 |
| | | | | 374/141 |
| 2002/0127007 A1 * | 9/2002 | Henrie | | F24H 9/2021 |
| | | | | 392/498 |
| 2004/0101025 A1 * | 5/2004 | Welker | | G01K 13/02 |
| | | | | 374/147 |
| 2004/0258130 A1 * | 12/2004 | Gotthold | | G01K 11/3213 |
| | | | | 374/208 |
| 2006/0185450 A1 * | 8/2006 | Kimura | | F04D 29/0413 |
| | | | | 73/865.9 |
| 2008/0277159 A1 * | 11/2008 | Liepold | | G01K 1/143 |
| | | | | 174/480 |
| 2009/0052498 A1 * | 2/2009 | Halpin | | G01K 7/04 |
| | | | | 374/179 |
| 2009/0066353 A1 * | 3/2009 | Devey | | G01D 11/245 |
| | | | | 324/756.03 |
| 2010/0037689 A1 * | 2/2010 | Arzberger | | B22D 2/00 |
| | | | | 73/295 |
| 2010/0091817 A1 * | 4/2010 | Wienand | | G01K 1/12 |
| | | | | 374/185 |
| 2010/0202489 A1 * | 8/2010 | McWilliams | | H01H 37/48 |
| | | | | 374/163 |
| 2012/0201270 A1 * | 8/2012 | Thompson | | G01K 11/08 |
| | | | | 374/160 |
| 2013/0167554 A1 * | 7/2013 | Parsons | | G01K 1/12 |
| | | | | 60/803 |
| 2013/0322489 A1 * | 12/2013 | Cuypers | | B22D 2/006 |
| | | | | 374/159 |

OTHER PUBLICATIONS

Conax Buffalo Technologies, Exhaust Gas Thermocouples 372A2221, Bulletin 6069 (May 2009).
Conax Buffalo Technologies, Exhaust Gas Thermocouples, Bulletin 6028 (Oct. 2002).

* cited by examiner

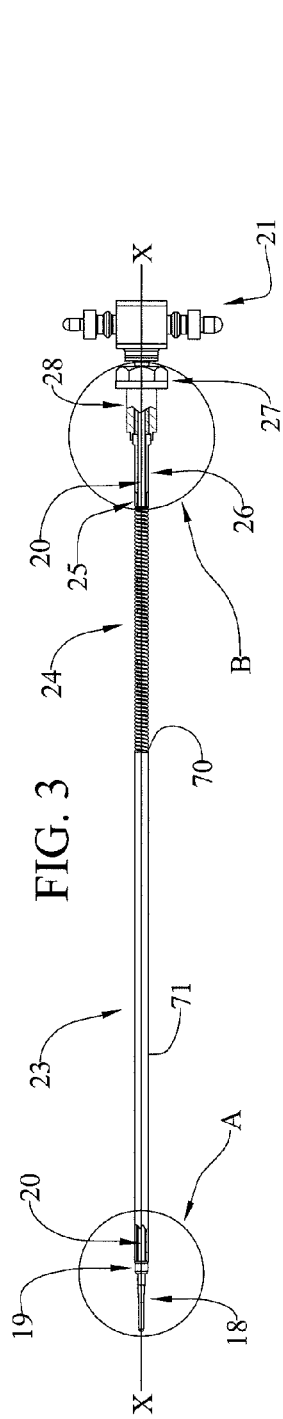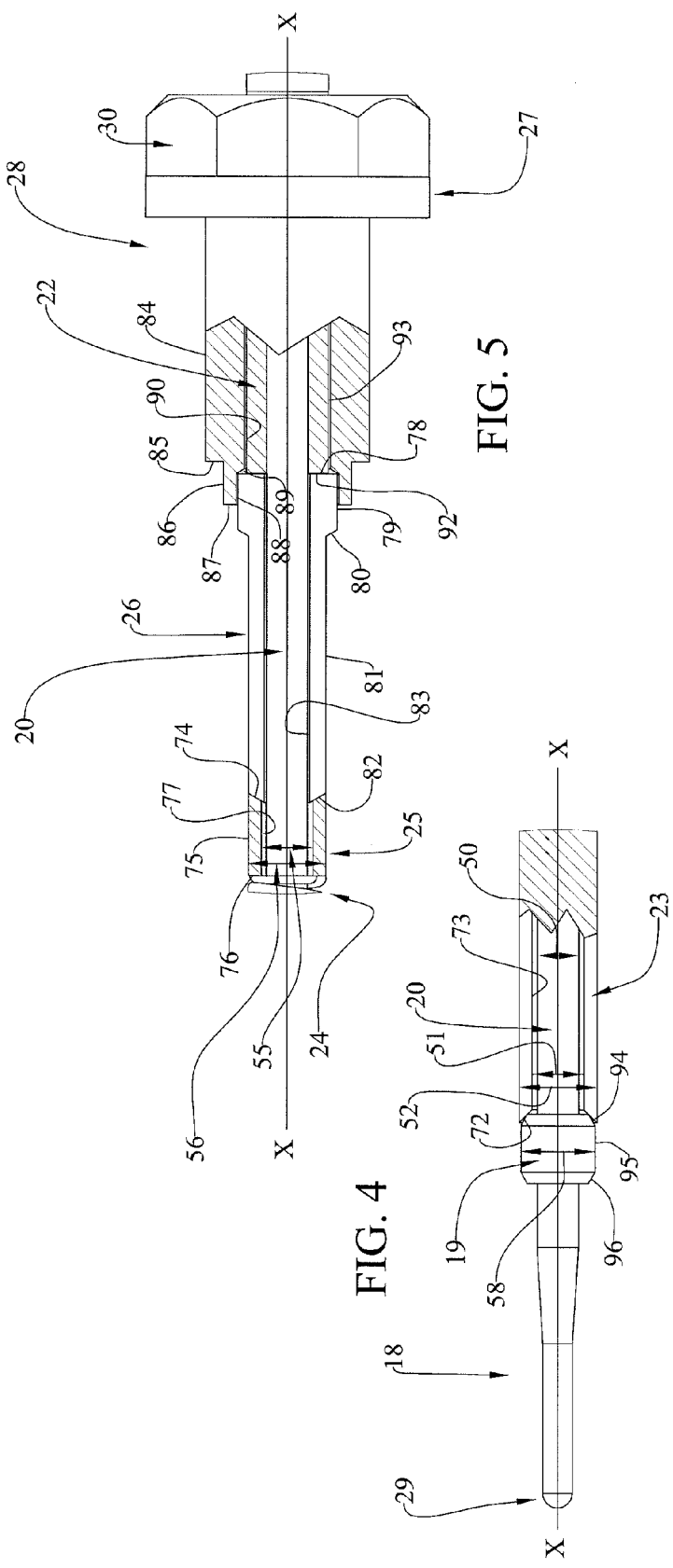
FIG. 3
FIG. 4
FIG. 5

SPRING LOADED EXHAUST GAS TEMPERATURE SENSOR ASSEMBLY

TECHNICAL FIELD

The present invention relates generally to the field of gas turbine sensors, and more particularly to an improved exhaust gas temperature sensor assembly.

BACKGROUND ART

Large frame power generation gas turbines that generate power from combustible fuels are often computer controlled through a series of complex algorithms and inputs from various types of sensors, including temperature sensors. Such sensor inputs play an important role in the efficiency and emissions performance of gas turbines.

Conventional large frame ground-based gas turbines use numerous exhaust gas thermocouples for control purposes. The number of sensors can range from sixteen on smaller output engines to as many as thirty on larger engines. Such thermocouples are typically installed in a radiation shield welded to the exhaust plenum of the turbine. The radiation shield design is intended to allow for easy replacement of the protected temperature sensor during maintenance or as a result of premature failure.

To avoid the problem of the temperature sensor seizing inside the radiation shield as a result of high temperature operating conditions, typically the sheath of the sensor and the radiation shield are made from different alloys.

SUMMARY OF THE INVENTION

With parenthetical reference to the corresponding parts, portions or surfaces of the disclosed embodiment, merely for the purposes of illustration and not by way of limitation, the present invention provides an improved temperature sensor assembly (15) comprising a temperature sensing probe (16) having a temperature sensing portion (18), a terminal portion (21), and an intermediate portion (20) between the temperature sensing portion and the terminal portion; a mounting element (28) in sliding engagement along a first axis (x-x) with the intermediate portion of the temperature sensing probe such that the temperature sensing probe is movable linearly relative to the mounting element in an axial direction; the mounting element configured to attach to an open tip thermowell (100) such that the temperature sensing portion of the probe is exposed to a process environment (104); the temperature sensing probe comprising a stop (19) configured to bear against a seat (108) in the thermowell; and a spring element (24) arranged between the stop and the mounting element and configured to bias the stop and the mounting element linearly away from each other in the axial direction. The temperature sensing probe may comprise a thermocouple or a resistance temperature detector. The open tip thermowell may comprise an exhaust gas turbine radiation shield. The mounting element may comprise a generally cylindrical fitting orientated about the first axis and having outwardly-facing threads (84); the radiation shield may comprise a generally cylindrical insertion opening (107) having inwardly-facing threads (109) corresponding to the outwardly-facing threads of the fitting; and the fitting of the mounting element may be configured to rotationally attach to the radiation shield at the insertion opening. The intermediate portion of the probe may comprise a generally cylindrical outer surface orientated about the first axis and having an intermediate outer diameter (50). The spring element may comprise a helical or coil compression spring orientated about the first axis around the intermediate portion of the probe and having a coil inner diameter greater than the intermediate outer diameter. The stop may comprise a generally cylindrical collar orientated about the first axis and having a collar outer diameter (58) greater than the spring inner diameter. The assembly may further comprise a spacer tube (23) orientated about the first axis around the intermediate portion of the probe and having a spacer inner diameter (51) greater than the intermediate outer diameter and a spacer outer diameter (52) greater than the coil inner diameter. The spacer tube may be positioned between the collar and the coil spring in the axial direction. The assembly may further comprise a second spacer tube (25) orientated about the first axis around the intermediate portion of the probe and positioned between the coil spring and the mounting element in the axial direction. The assembly may further comprise a split bushing (26) orientated about the first axis around the intermediate portion of the probe and positioned between the second spacer tube and the mounting element. The bushing may be removable to unload the spring. The seat may comprise an inwardly-facing frusto-conical surface (108) orientated about the first axis and the collar may comprise an outwardly-facing frusto-conical surface (96) orientated about the first axis and configured to bear against the inwardly-facing frusto-conical surface of the seat. The collar may comprise a second outwardly-facing frusto-conical surface (94) orientated about the first axis and the spacer tube may comprise an inwardly-facing frusto-conical surface (72) orientated about the first axis and configured to bear against the outwardly-facing frusto-conical surface of the collar. The fitting may comprise a counter bore (88, 89) configured to receiving an end portion (78, 79) of the split bushing. The split bushing may comprise an outwardly-facing frusto-conical surface (82) orientated about the first axis and the second spacer tube may comprise an inwardly-facing frusto-conical surface (74) orientated about the first axis and configured to bear against the outwardly-facing frusto-conical surface of the split bushing.

The temperature sensing probe may be movable linearly relative to the mounting element in an axial direction between a first assembled position (FIGS. 3-5) and a second installed position (FIGS. 6-10). The intermediate portion of the probe may comprise a support tube (22) orientated about the first axis and fixed to the terminal portion and the mounting element may be in sliding engagement along the first axis with the support tube of the intermediate portion of the temperature sensing probe. The assembly may further comprise a spacer tube (23) orientated about the first axis around the intermediate portion of the probe and positioned between the collar and the coil spring in the axial direction; a second spacer tube (25) orientated about the first axis around the intermediate portion of the probe and positioned between the coil spring and the mounting element in the axial direction; a split bushing (26) orientated about the first axis around the intermediate portion of the probe and positioned between the second spacer tube and the mounting element; and a distance (40) between an end face (92) of the support tube and a corresponding end face (78) of the bushing may vary in length in the axial direction with movement of the temperature sensing probe between the first assembled position and the second installed position.

The stop may be between the temperature sensing portion and the terminal portion. The stop may comprise a tip of the temperature sensing portion. The assembly may further comprise a turbine connected to the open tip thermowell.

In another aspect the invention provides a method of measuring the temperature of an exhaust gas comprising the steps of providing an open tip thermowell having a seat; providing a temperature sensor assembly comprising: a temperature sensing probe having a temperature sensing portion, a terminal portion, and an intermediate portion between the temperature sensing portion and the terminal portion; a mounting element in sliding engagement along a first axis with the intermediate portion of the temperature sensing probe such that the temperature sensing probe is movable linearly relative to the mounting element in an axial direction; the mounting element configured to attach to the open tip thermowell such that the temperature sensing portion of the probe is exposed to a process environment; the temperature sensing probe comprising a stop configured to bear against the seat in the open tip thermowell; and a spring element arranged between the stop and the mounting element and configured to bias the stop and the mounting element linearly away from each other in the axial direction; installing the sensor assembly in the open tip thermowell such that the spring element is compressed and the stop bears against the seat in the open tip thermowell; and sensing temperature.

BRIEF DESCRIPTION OF THE DRAWINGS

FIG. 3 is a partial cross-sectional side view of the sensor assembly shown in FIG. 1.

FIG. 4 is an enlarged detailed view of the sensing end of the sensor assembly shown in FIG. 3, taken generally within the indicated circle A of FIG. 3.

FIG. 5 is an enlarged detailed view of the mounting portion of the sensor assembly shown in FIG. 3, taken generally within the indicated circle B of FIG. 3.

DESCRIPTION OF EMBODIMENTS

Figure 1:
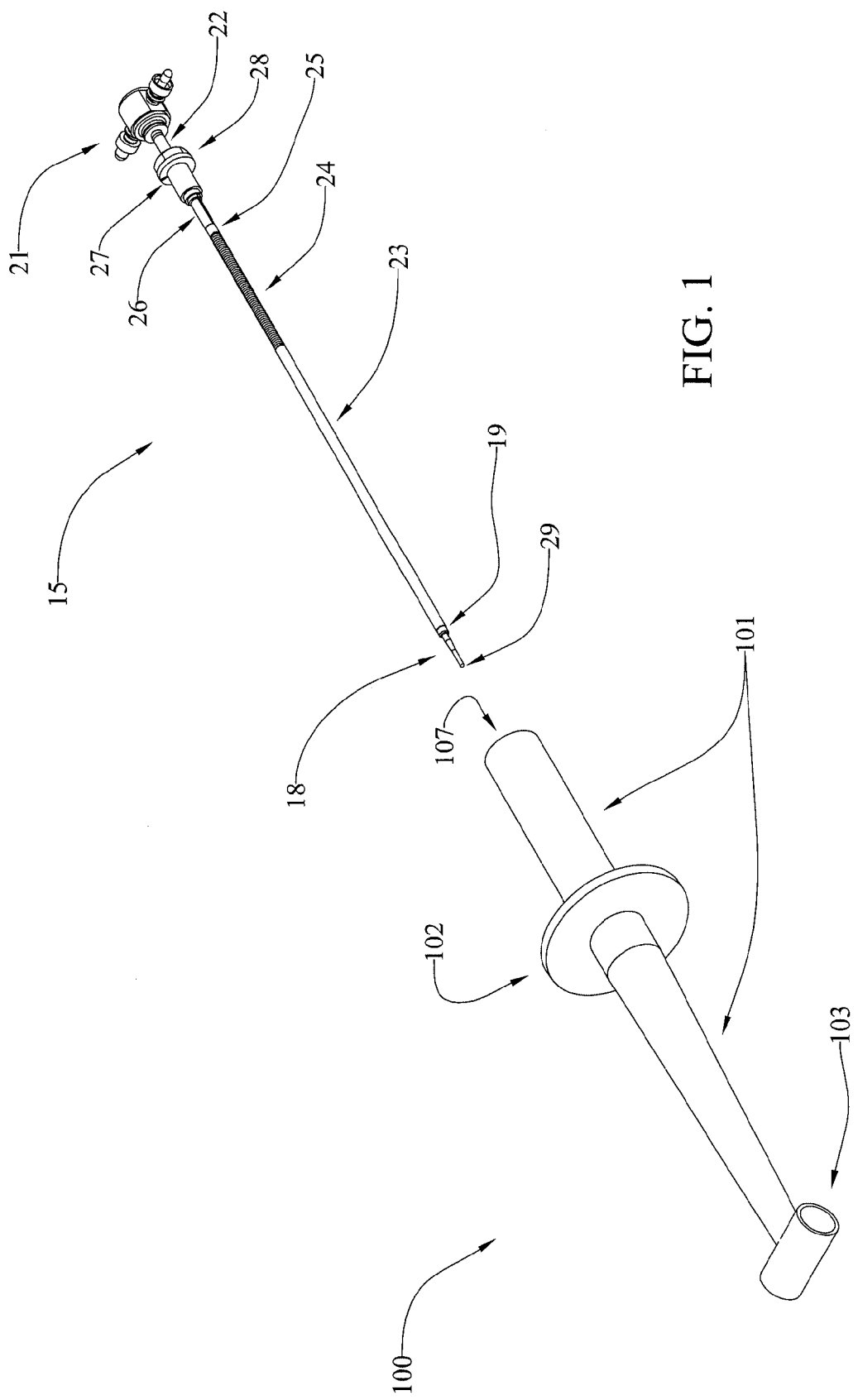
FIG. 1 is a perspective view of the improved sensor assembly and a conventional radiation shield into which it is installed when in use on a gas turbine.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Referring now to the drawings, and more particularly to FIG. 1 thereof, this invention provides an improved exhaust gas temperature sensor assembly, the presently preferred embodiment of which is generally indicated at 15. As shown, sensor assembly 15 is configured for use with conventional radiation shield 100. Other types of radiation shields may be used as alternatives.

As shown, radiation shield 100 includes generally hollow conical body 101, transversely extending cylindrical exhaust sampling tube 103 and annular flange 102, by which the radiation shield is welded to an existing large scale gas turbine such that exhaust flow of the turbine passes through cylindrical passage 104 in cylindrical exhaust sampling tube 103, the temperature of which is monitored by probe 16. As shown in FIGS. 1 and 7-10, radiation shield 100 has a longitudinally extending inner cylindrical bore 105 into which sensor assembly 15 is inserted. At one end inner cylindrical bore 105 has tip opening 106 through which tip 29 of probe 16 projects into exhaust passage 104 of sampling tube 103 and at the other end inner cylindrical bore 105 has insertion opening 107 from which terminal head 21 of probe 16 projects.

As shown, sensor assembly 15 generally includes temperature sensing probe 16 and a dampening assembly, generally indicated at 17. In this embodiment temperature sensing probe 16 comprises a generally cylindrical thermocouple. As shown, thermocouple 16 is orientated about axis x-x and includes sensing portion 18, having tip 29, intermediate portion 20, with sealing collar 19 at one end and support tube 22 at the other end, and terminal head 21.

As shown, terminal head 21 generally includes a ceramic insulated junction box having terminals adapted to connect to cabling by compression fitting. Terminal head 21 has two different sized studs for proper installation and enables a convenient, stress-free orientation of the thermocouple junction box as it relates to the mating cable. Other types of terminal heads may be used as alternatives.

Intermediate portion 20 extends from terminal end 21 to sealing collar 19 and generally supports dampening assembly 17. As shown, intermediate portion 20 is a generally elongated cylindrical member having a generally constant outside diameter along its central length.

Figure 8:
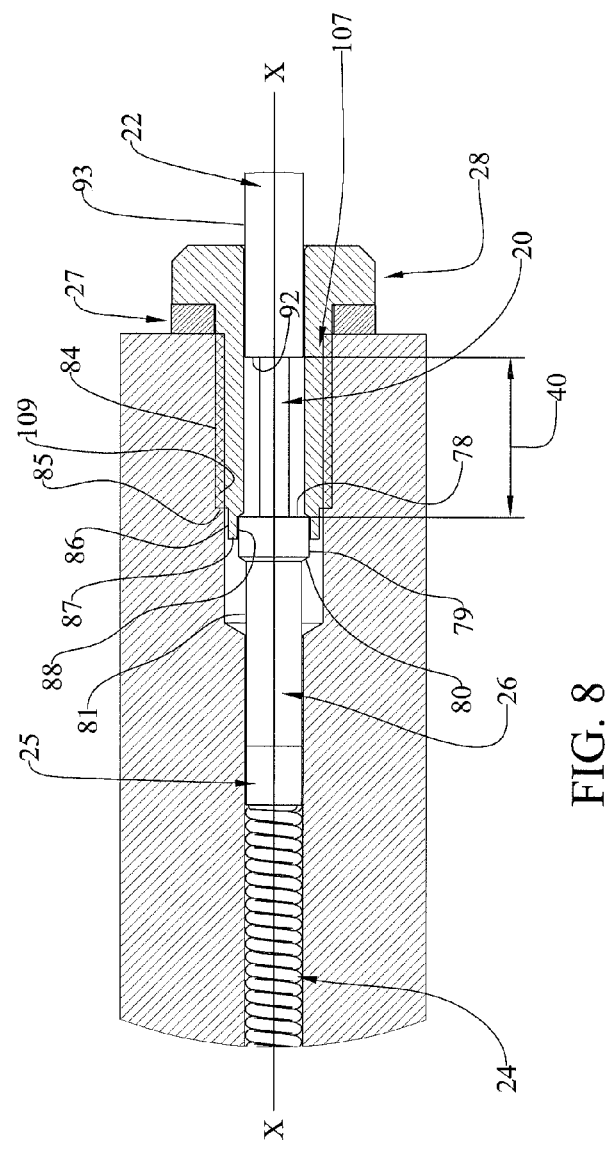
FIG. 8 is an enlarged detailed view of the mounting end of the sensor assembly and radiation shield shown in FIG. 7, taken generally within the indicated circle C of FIG. 7.

However, adjacent terminal head 21, intermediate portion 20 of probe 16 includes a widened support tube 22 having a diameter greater than most of intermediate portion 20. Support tube 22 is provided to better support the weight of terminal head 21 when cantilevered out the end of mounting fixture 28 and radiation shield 100 when in use. With reference to FIGS. 5 and 8, support tube 22 is generally defined by outwardly-facing horizontal cylindrical surface 93 and leftwardly-facing vertical annular surface 92. Support tube 22 is welded or fixed at its right end face to terminal head 21 of probe 16.

Figure 10:
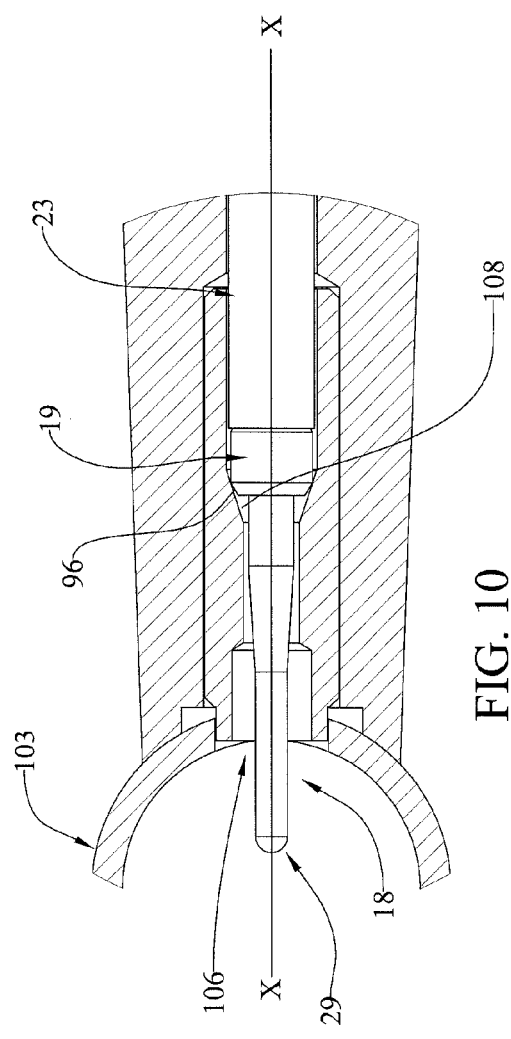
FIG. 10 is an enlarged detailed view of the sensing end of the sensor assembly and radiation shield shown in FIG. 9, taken generally within the indicated circle D of FIG. 7.

Adjacent sensing portion 18, intermediate portion 20 includes a widened sealing collar having a diameter greater than most of intermediate portion 20 and chamfered outside edges. With reference to FIGS. 4 and 10, collar 19 is generally defined by rightwardly and outwardly-facing frusto-conical surface 94, outwardly-facing horizontal cylindrical surface 95, and leftwardly and outwardly-facing frusto-conical surface 96. Outside diameter 58 of cylindrical surface 95 is about the same as outside diameter 52 of spacer tube 23. In this embodiment collar 19 is welded to thermocouple 16.

Sensing portion 18 extends beyond sealing collar 19 on the opposite end from terminal head 21. As shown, sensing portion 18 narrows to tip 29. Sensing portion 18 is configured to extend into the environment from which temperature readings are desired.

Figure 2:
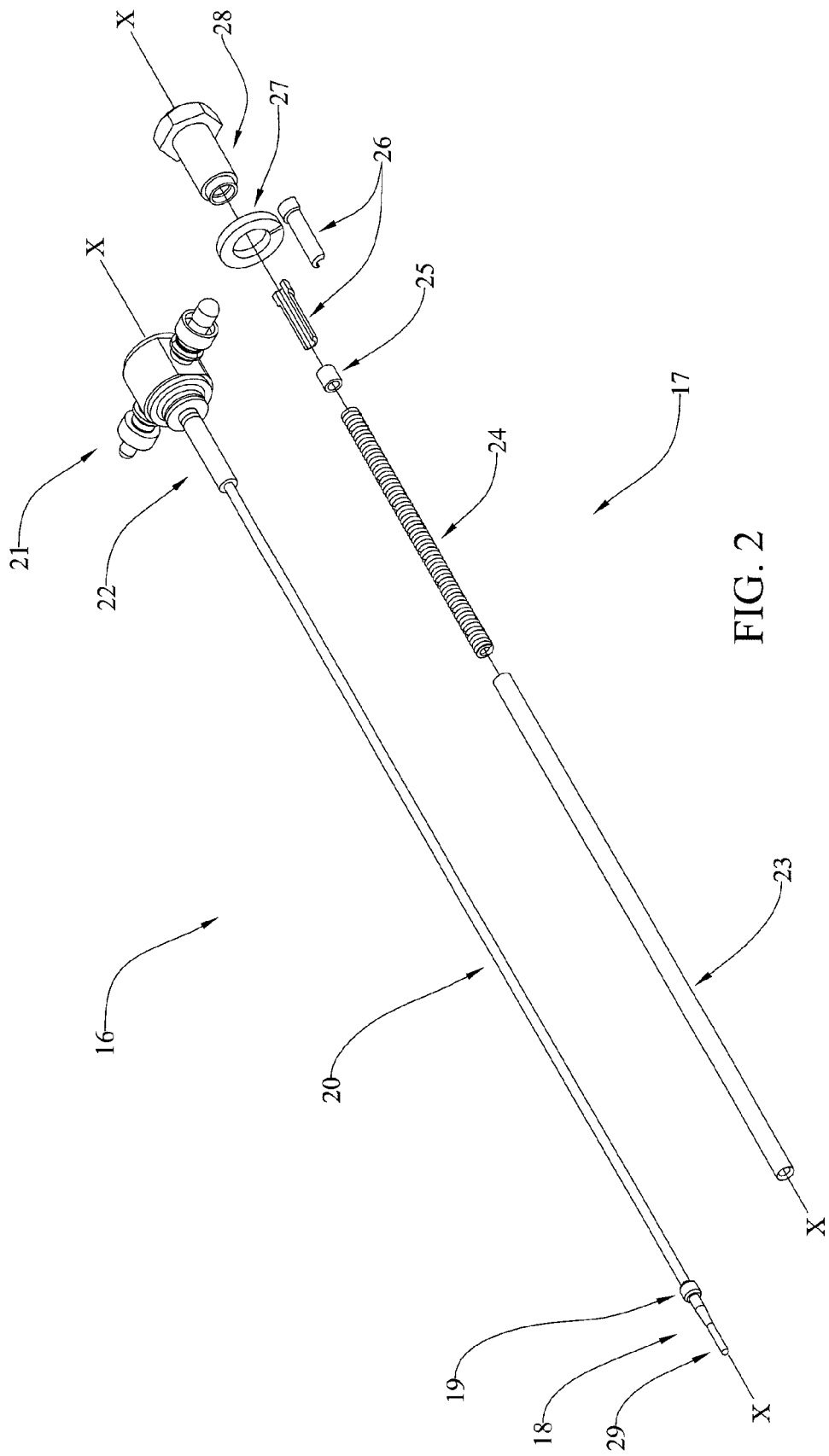
FIG. 2 is an exploded view of the sensor assembly shown in FIG. 1.
Figure 6:
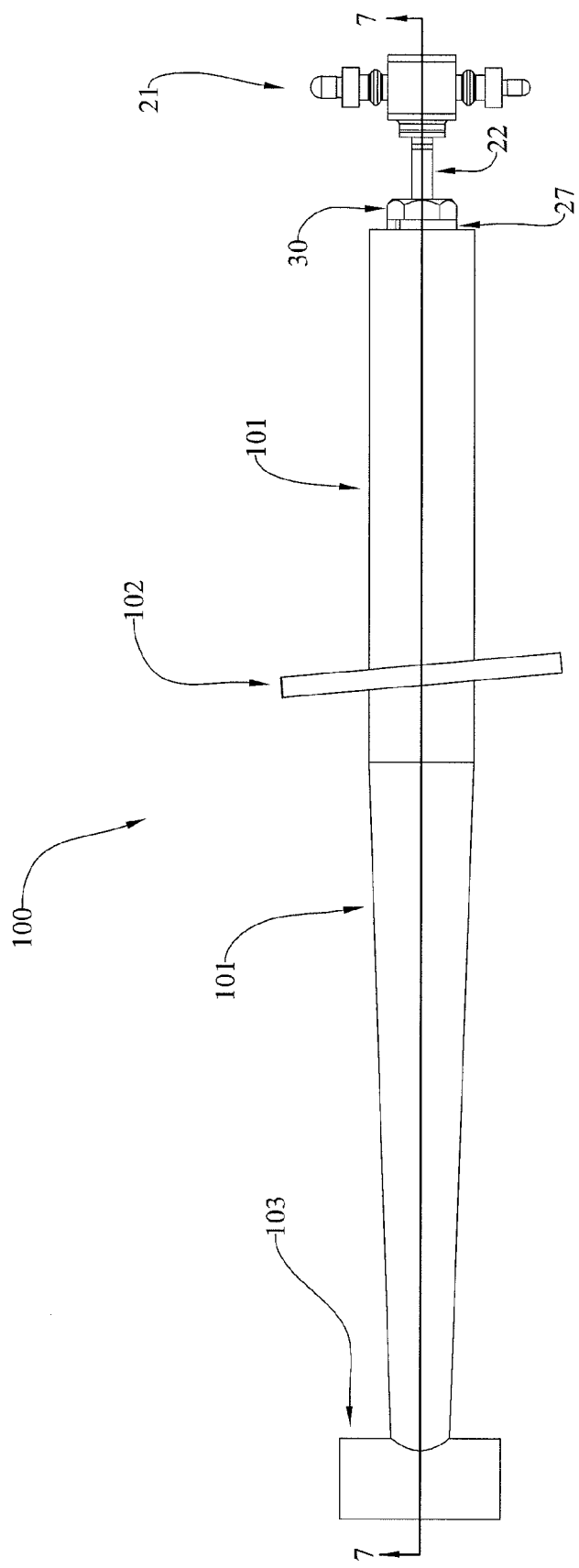
FIG. 6 is a side view of the sensor assembly shown in FIG. 1 installed in the radiation shield shown in FIG. 1.

As shown in FIG. 2, dampening assembly 17 is generally concentric with probe 16 and includes spacer tube 23, coil spring 24, spacer tube 25, split bushing 26, spring style lock washer 27 and threaded fitting 28.

As shown in FIGS. 3-5, spacer tube 23 is generally a specially-configured hollow cylindrical member or sleeve oriented along axis x-x and bounded by rightwardly-facing annual vertical surface 70, outwardly-facing horizontal cylindrical surface 71, leftwardly and inwardly-facing frusto-conical surface 72, and inwardly-facing horizontal cylindrical surface 73, joined at its right marginal end to the inner marginal end to surface 70. Inner diameter 51 of spacer 23 is slightly greater than outer diameter 50 of intermediate portion 20 of thermocouple 16. Thus, spacer 23 is in sliding engagement with the intermediate portion 20 of thermocouple 16 along axis x-x.

Coil spring 24 is a high temperature compression spring that is compressed between fitting 28 and sealing collar 19 when assembled. Spring 24 has an inner diameter that is generally the same as inner diameter 51 of spacer 23 and has an outer diameter that is also generally the same as outer diameter 52 of spacer 23. Thus, like spacer 23, spring 24 is in sliding engagement with intermediate portion 20 of thermocouple 16.

Spacer tube 25 is generally a specially-configured hollow cylindrical member or sleeve elongated along axis x-x, and bounded by rightwardly and inwardly-facing frusto-conical surface 74, outwardly-facing horizontal cylindrical surface 75, leftwardly-facing vertical annular surface 76, and inwardly-facing horizontal cylindrical surface 77, joined at its right marginal end to the inner marginal end of surface 74. Inner diameter 55 of spacer tube 25 is about the same as inner diameter 51 of spacer tube 23 and outer diameter 56 of spacer tube 25 is about the same as outer diameter 52 of spacer tube 23. Thus, like spacer 23, spacer tube 25 is in sliding engagement along intermediate portion 20 of thermocouple 16 along axis x-x.

As shown in FIG. 5, bushing 26 is generally a specially configured hollow cylindrical member or sleeve elongated along axis x-x and split in the longitudinal direction in two halves that may be separated from each other during assembly or disassembly to unload spring 24. As shown, bushing 26 is bounded by rightwardly-facing vertical annular surface 78, outwardly-facing horizontal cylindrical surface 79, outwardly and leftwardly-facing frusto-conical surface 80, outwardly-facing horizontal cylindrical surface 81, leftwardly and outwardly-facing frusto-conical surface 82, and inwardly-facing horizontal cylindrical surface 83, joined at its right marginal end to the inner marginal end of surface 78.

Fitting 28 is a generally a specially-configured hollow cylindrical member elongated along axis x-x. As shown, fitting 28 includes outwardly-facing horizontal threaded cylindrical surface 84, leftwardly-facing vertical annular surface 85, outwardly-facing horizontal cylindrical surface 86, leftwardly-facing vertical annular surface 87, inwardly-facing horizontal cylindrical surface 88, leftwardly-facing vertical annular surface 89, and inwardly-facing horizontal cylindrical surface 90.

As shown, intermediate portion 20, including support tube 22, of thermocouple 16 extends through the inner hollow cylindrical bore in fitting 28 defined by inner cylindrical surface 90. The opening defined by surface 90 in fitting 28 and the outer cylindrical surface 93 of mounting tube 22 are dimensioned such that intermediate portion 20 of thermocouple 16 is in sliding engagement along axis x-x with fitting 28. However, outer cylindrical surface 79 of bushing 26 has a diameter that it is too large to fit through the opening defined by surface 90 in fitting 28. Similarly, terminal head 21 on the opposite side of fitting 28 from bushing 26 is too large to fit through the opening defined by surface 90 in fitting 28. However, terminal head 21, and thus probe 16, can move linearly along axis x-x a given distance 40 relative to fitting 28 between a first assembled position, shown in FIG. 5, and a second installed position, shown in FIG. 8. Surface 92 of support tube 22 and terminal head 21 act as a hard stop against movement of bushing 26 and fitting 28 away from sealing collar 19 beyond a certain distance.

As shown, the right portion of fitting 28 includes a hexagonal shaped nut portion 30 adapted to be engaged with a wrench or other suitable tightening tool. Nut portion 30 is also sized so that it is too large to fit through insertion opening 107 in radiation shield 100.

Spring 24 is operatively compressed between fitting 28 and sealing collar 19. In particular, the left edge of spring 24 bears against right annular surface 70 of spacer tube 23, and the left frusto-conical surface 72 of spacer tube 23 in turn bears against the right frusto-conical surface 94 of sealing collar 19 of probe 16. The right edge of spring 24 bears against left annular surface 76 of spacer tube 25, and the right frusto-conical surface 74 of spacer tube 25 in turn bears against left frusto-conical surface 82 of split bushing 26, and a portion of the right annular surface 78 of bushing 26 in turn bears against left annular surface 89 of fitting 28. Thus, spring 24 ultimately acts between fitting 28 and sealing collar 19, biasing fitting 28 away from sealing collar 19 in the axial direction.

When assembly 15 is assembled, but not yet installed within radiation shield 100, as shown in FIG. 5, spring 24 is slightly compressed due to left annular surface 92 of support tube 22 and the left face of terminal 21 acting as a hard stop to bushing 26 and fixture 28 sliding further along probe 16 away from collar 19. Thus, the relative lengths of the elements of assembly 15 and support tube 22 are such that no gap is provided between left annular surface 92 of support tube 22 and right annular surface 78 of bushing 26 when assembled but not installed. Because surface 92 acts as a hard stop to movement of probe 16 relative to fixture 28 beyond this assembled position, spring 24 is held in compression. One advantage of this arrangement is that a more constant force may be applied over the operating range of linear movement of probe 16 relative to fixture 28 between the assembled position shown in FIG. 5 and the installed position shown in FIG. 8. However, it is contemplated that the spring force to displacement characteristics of spring 24 and/or the relative lengths of the elements could be varied so that spring 24 is not compressed at all in the assembled position or so that the amount of such compression is adjusted as desired.

Figure 7:
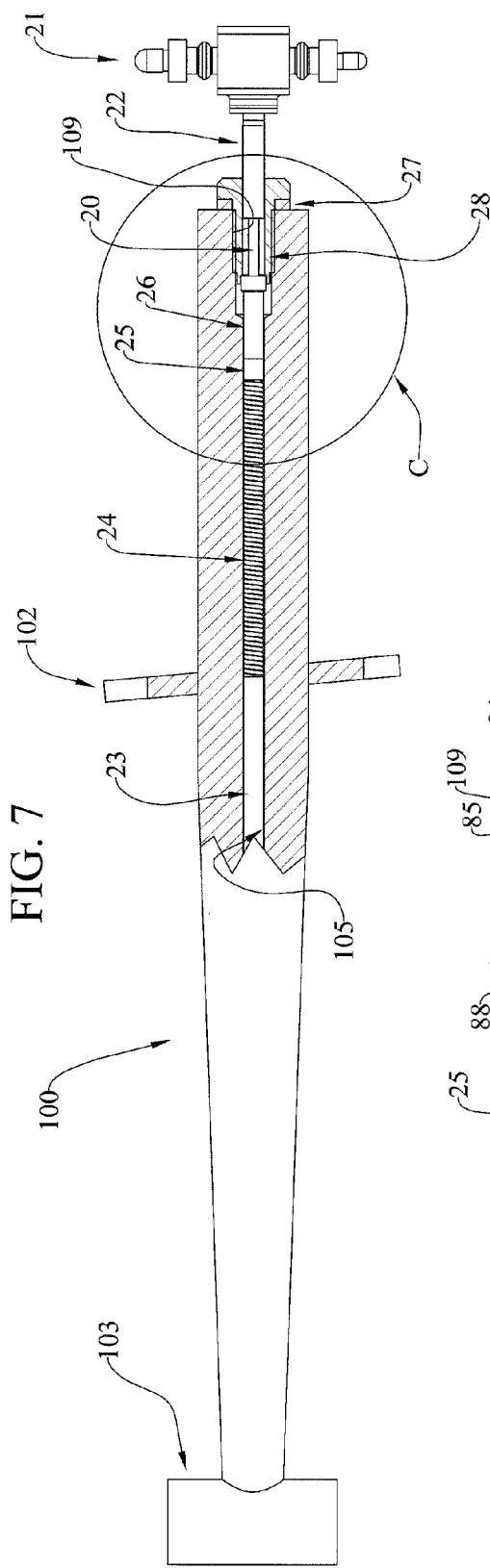
FIG. 7 is a partial vertical cross-sectional view of the sensor assembly and radiation shield shown in FIG. 6, taken generally on line 7-7 of FIG. 6.

As shown in FIGS. 7 and 8, insertion opening 107 of radiation shield 100 includes inwardly-facing threaded cylindrical surface 109. The threads on surface 109 are threaded to correspond to the outwardly-facing threads of surface 84 of fitting 28. Thus, sensor assembly 15 can be inserted into bore 105 of shield 100 and nut portion 30 of fitting 28 then rotated about axis x-x relative to shield 100 until nut portion 30 of fitting 28 abuts the right end face of radiation shield 100. This tightening action attaches fitting 28 to the top end of shield 100 so it does not move linearly relative to shield 100 and further compresses spring 24.

Figure 9:
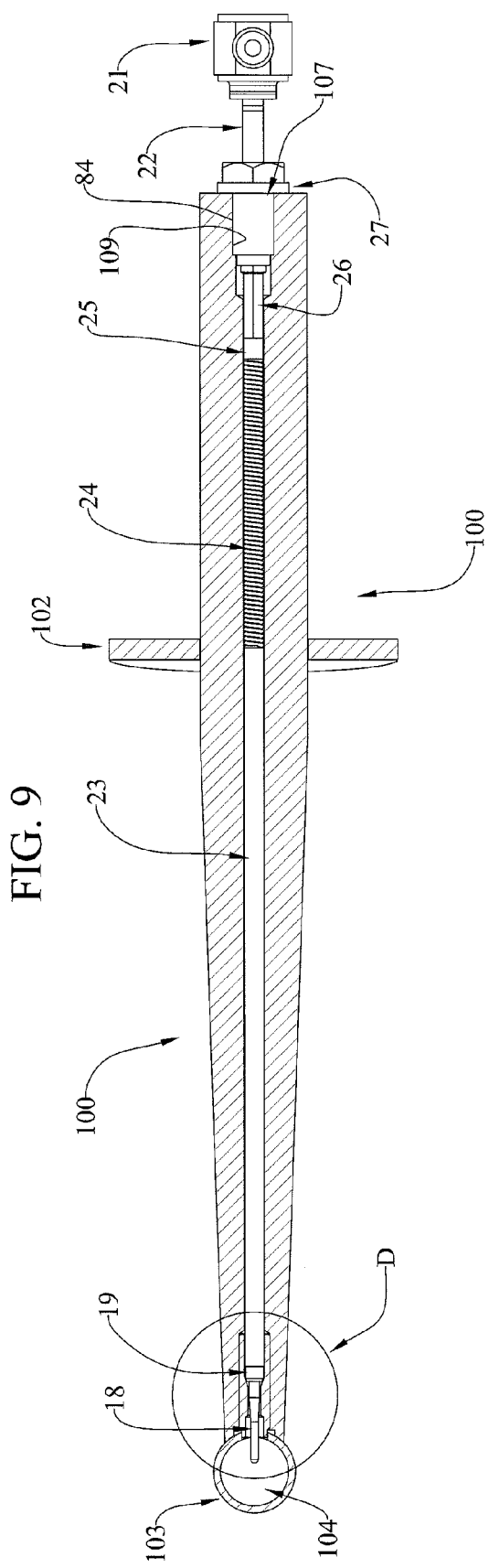
FIG. 9 is a horizontal cross-sectional view of the sensor assembly and radiation shield shown in FIG. 6, taken generally on line 7-7 of FIG. 6.

With fitting 28 properly attached to shield 100, as shown in FIGS. 9-10, thermocouple 16 extends into bore 105 such that collar 19 abuts seat 108 of shield 100. As shown, seat 108 is a rightwardly and inwardly-facing frusto-conical surface. Left frusto-conical surface 96 of collar 19 is thereby configured to abut against surface 108 of shield 100 in sealing engagement.

When first installed and without increased operating temperatures, spring 24 is in its most compressed operational state and probe 16 is in an installed linear position relative to fitting 28 and radiation shield 100, as shown in FIG. 8. When temperatures increases, and shield 100 expands in an amount greater than probe 16 due to differences in their respective coefficients of thermal expansion, spring 24 provides a spring force that biases collar 19 against and in sealing engagement with seat 108 of shield 100. With reference to FIG. 9, spring 24 provides a spring force leftward so as to close any gap formed between collar 19 and seat 108 and maintain constant contact between collar 19 and seat 108 during operating conditions. Thus, spring 23 will tend to expand as necessary to maintain constant contact between sealing collar 19 and radiation shield 100. Dampening assembly 17 thereby maintains a constant union of contact between parts to protect from vibration that would otherwise occur from a variation in the relative length of shield 100 and thermocouple 16 caused by high temperatures and different relative coefficients of thermal expansion.

As shown in FIG. 8, the relative lengths of the elements of assembly 15 are such that gap 40 is provided between left annular surface 92 of support tube 22 and right annular surface 78 of bushing 26 when assembly 15 is installed within shield 100. Because terminal head 21 and surface 92 act as a hard stop to movement of probe 16 relative to fixture 28 beyond the assembled position, in this embodiment gap 40 is greater than the effective difference in thermal expansion of probe 16 and radiation shield 100 under intended operating conditions. Distance 40 correlates to the spring travel range or displacement range of spring 24 between the assembled position shown in FIGS. 3-5 and the installed position shown in FIGS. 6-10. Assembly 15 is configured to have enough spring travel to compensate for any relative differences in expansion of shield 100 and probe 16.

Thus, high temperature compression spring 24 is built into the sensor sheath so that spring 24 dampens vibration and keeps temperature sensor tip 29 stable within radiation shield 100 by ensuring a continuity of contact between stop 19 on the probe and seat 108 of radiation shield 100.

A number of benefits result from the improved assembly. First, because radiation shield 100 and sensor sheath 16 may be formed of different materials and have different coefficients of thermal expansion, at operating temperatures bore 105 of radiation shield 100 may expand in length more than sensor sheath 16, thereby creating a gap between seat 108 of radiation shield 100 and sealing collar 19 on sensor sheath 16. This gap can leave enough room for the sensor to vibrate due to turbine gas flows and input vibrations from the engine. And such vibration may break the tip of the sensor, causing the sensor to prematurely fail. With the improved assembly, spring 24 is configured to keep sealing collar 19 of temperature sensor 16 properly seated against radiation shield 100, even at high temperatures, thereby reducing any gap between seat 108 of radiation shield 100 and collar 19 on sensor sheath 16. This has been found to dampen the vibration of the sensor and to keep temperature sensor tip 29 stable within radiation shield 100.

The present invention contemplates that many changes and modifications may be made. Therefore, while the presently-preferred form of a spring loaded exhaust gas temperature sensor assembly has been shown and described, and several modifications and alternatives discussed, persons skilled in this art will readily appreciate that various additional changes and modifications may be made without departing from the spirit of the invention, as defined and differentiated by the following claims.

What is claimed is:

1. A temperature sensor assembly comprising:
a temperature sensing probe having a temperature sensing portion, a terminal portion, and an intermediate portion between said temperature sensing portion and said terminal portion;
a mounting element in sliding engagement along a first axis with said intermediate portion of said temperature sensing probe such that said temperature sensing probe is movable linearly relative to said mounting element in an axial direction;
said mounting element configured to attach to an open tip thermowell having a different coefficient of thermal expansion than said temperature sensing probe, and such that said mounting element does not move linearly relative to said open tip thermowell, such that said temperature sensing portion of said probe is exposed to a process environment, and such that said thermowell will expand in an amount different than said temperature sensing probe in response to temperatures in said process environment;
said temperature sensing probe comprising a stop configured to bear against a seat in said thermowell; and
a spring element arranged between said stop and said mounting element and configured to bias said stop and said mounting element linearly away from each other in said axial direction;
whereby said temperature sensing probe is movable linearly relative to said mounting element in said axial direction through a displacement range in which said spring element will compensate for said relative differences in expansion of said temperature sensing probe and said thermowell from said temperatures in said process environment.

2. The assembly set forth in claim 1, wherein said temperature sensing probe comprises a thermocouple.

3. The assembly set forth in claim 1, wherein said temperature sensing probe comprises a resistance temperature detector.

4. The assembly set forth in claim 1, wherein said open tip thermowell comprises an exhaust gas turbine radiation shield.

5. The assembly set forth in claim 4, wherein;
said mounting element comprises a generally cylindrical fitting orientated about said first axis and having outwardly-facing threads;
said radiation shield comprises a generally cylindrical insertion opening having inwardly-facing threads corresponding to said outwardly-facing threads of said fitting; and
said fitting of said mounting element is configured to rotationally attach to said radiation shield at said insertion opening.

6. The assembly set forth in claim 1, wherein said intermediate portion of said probe comprises a generally cylindrical outer surface orientated about said first axis and having an intermediate outer diameter.

7. The assembly set forth in claim 6, wherein said spring element comprises a helical or coil compression spring orientated about said first axis around said intermediate portion of said probe and having a coil inner diameter greater than said intermediate outer diameter.

8. The assembly set forth in claim 7, wherein said stop comprises a generally cylindrical collar orientated about said first axis and having a collar outer diameter greater than said spring inner diameter.

9. The assembly set forth in claim 8, and further comprising a spacer tube orientated about said first axis around said intermediate portion of said probe and having a spacer inner diameter greater than said intermediate outer diameter and a spacer outer diameter greater than said coil inner diameter.

10. The assembly set forth in claim 9, wherein said spacer tube is positioned between said collar and said coil spring in said axial direction.

11. The assembly set forth in claim 10, and further comprising a second spacer tube orientated about said first axis around said intermediate portion of said probe and positioned between said coil spring and said mounting element in said axial direction.

12. The assembly set forth in claim 11, and further comprising a split bushing orientated about said first axis around said intermediate portion of said probe and positioned between said second spacer tube and said mounting element.

13. The assembly set forth in claim 12, wherein said bushing is removable to unload said spring.

14. The assembly set forth in claim 13, wherein said seat comprises an inwardly-facing frusto-conical surface orientated about said first axis and wherein said collar comprises an outwardly-facing frusto-conical surface orientated about said first axis and configured to bear against said inwardly-facing frusto-conical surface of said seat.

15. The assembly set forth in claim 14, wherein said collar comprises a second outwardly-facing frusto-conical surface orientated about said first axis and said spacer tube comprises an inwardly-facing frusto-conical surface orientated about said first axis and configured to bear against said outwardly-facing frusto-conical surface of said collar.

16. The assembly set forth in claim 15, wherein said mounting element comprises a generally cylindrical fitting and said fitting comprises a counter bore configured to receive an end portion of said split bushing.

17. The assembly set forth in claim 16, wherein said split bushing comprises an outwardly-facing frusto-conical surface orientated about said first axis and said second spacer tube comprises an inwardly-facing frusto-conical surface orientated about said first axis and configured to bear against said outwardly-facing frusto-conical surface of said split bushing.

18. The assembly set forth in claim 1, wherein said temperature sensing probe is movable linearly relative to said mounting element in an axial direction between a first assembled position and a second installed position.

19. The assembly set forth in claim 18, wherein said intermediate portion of said probe comprises a support tube orientated about said first axis and fixed to said terminal portion and said mounting element is in sliding engagement along said first axis with said support tube of said intermediate portion of said temperature sensing probe.

20. The assembly set forth in claim 19, and further comprising:
   a spacer tube orientated about said first axis around said intermediate portion of said probe and positioned between said collar and said coil spring in said axial direction;
   a second spacer tube orientated about said first axis around said intermediate portion of said probe and positioned between said coil spring and said mounting element in said axial direction;
   a split bushing orientated about said first axis around said intermediate portion of said probe and positioned between said second spacer tube and said mounting element; and
   wherein a distance between an end face of said support tube and a corresponding end face of said bushing varies in length in said axial direction with movement of said temperature sensing probe between said first assembled position and said second installed position.

21. The assembly set forth in claim 1, wherein said stop is between said temperature sensing portion and said terminal portion.

22. The assembly set forth in claim 1, wherein said stop comprises a tip of said temperature sensing portion.

23. The assembly set forth in claim 1, and further comprising a turbine connected to said open tip thermowell.

24. A method of measuring the temperature of an exhaust gas comprising the steps of:
   providing an open tip thermowell having a seat;
   providing a temperature sensor assembly comprising:
      a temperature sensing probe having a temperature sensing portion, a terminal portion, and an intermediate portion between said temperature sensing portion and said terminal portion;
      a mounting element in sliding engagement along a first axis with said intermediate portion of said temperature sensing probe such that said temperature sensing probe is movable linearly relative to said mounting element in an axial direction;
      said mounting element configured to attach to an open tip thermowell having a different coefficient of thermal expansion than said temperature sensing probe, and such that said mounting element does not move linearly relative to said open tip thermowell, such that said temperature sensing portion of said probe is exposed to a process environment, and such that said thermowell will expand in an amount different than said temperature sensing probe in response to temperatures in said process environment
      said temperature sensing probe comprising a stop configured to bear against said seat in said open tip thermowell; and
      a spring element arranged between said stop and said mounting element and configured to bias said stop and said mounting element linearly away from each other in said axial direction;
   installing said sensor assembly in said open tip thermowell such that said spring element is compressed and said stop bears against said seat in said open tip thermowell and such that said temperature sensing probe is movable linearly relative to said mounting element in said axial direction through a displacement range in which said spring element will compensate for said relative differences in expansion of said temperature sensing probe and said thermowell from said temperatures in said process environment; and
   sensing temperature.

25. The method set forth in claim 24, wherein said temperature sensing probe comprises a thermocouple.

26. The method set forth in claim 24, wherein said open tip thermowell comprises an exhaust gas turbine radiation shield.

27. The method set forth in claim 26, wherein;

said mounting element comprises a generally cylindrical fitting orientated about said first axis and having outwardly-facing threads;

said radiation shield comprises a generally cylindrical insertion opening having inwardly-facing threads corresponding to said outwardly-facing threads of said fitting; and said fitting of said mounting element is configured to rotationally attach to said radiation shield at said insertion opening.

28. The method set forth in claim 24, wherein said temperature sensing probe is movable linearly relative to said mounting element in an axial direction between a first assembled position and a second installed position.

29. The method set forth in claim 28, wherein said intermediate portion of said probe comprises a support tube orientated about said first axis and fixed to said terminal portion and said mounting element is in sliding engagement along said first axis with said support tube of said intermediate portion of said temperature sensing probe.

30. The method set forth in claim 29, and further comprising:

a spacer tube orientated about said first axis around said intermediate portion of said probe and positioned between said collar and said coil spring in said axial direction;

a second spacer tube orientated about said first axis around said intermediate portion of said probe and positioned between said coil spring and said mounting element in said axial direction;

a split bushing orientated about said first axis around said intermediate portion of said probe and positioned between said second spacer tube and said mounting element; and wherein a distance between an end face of said support tube and a corresponding end face of said bushing varies in length in said axial direction with movement of said temperature sensing probe between said first assembled position and said second installed position.

* * * * *